United States Patent [19]
Repice et al.

[11] Patent Number: 5,632,726
[45] Date of Patent: May 27, 1997

[54] DEVICE FOR USE ON A TRACTION MACHINE TO TREAT CARPAL TUNNEL SYNDROME AND OTHER PROBLEMS OF THE WRIST

[76] Inventors: Ronald M. Repice, 640 Georgetown Rd.; Ronald M. Repice, II, 299 Stanton Ct., both of Glen Mills, Pa. 19342

[21] Appl. No.: 554,117

[22] Filed: Nov. 6, 1995

[51] Int. Cl.$^6$ .................................................. A61F 5/00
[52] U.S. Cl. ............................ 602/36; 602/32; 601/33; 606/241
[58] Field of Search ............................ 602/32–36; 601/5, 601/26, 23, 33, 40; 128/845, 878, 879, 881; 606/241; 5/623, 646, 647; 482/44

[56] References Cited

U.S. PATENT DOCUMENTS

| | | | |
|---|---|---|---|
| 2,374,163 | 4/1945 | Burchsted | 602/34 |
| 2,633,124 | 3/1953 | Yellin | 602/36 |
| 3,087,489 | 4/1963 | Gilbert et al. | 602/33 |
| 4,089,330 | 5/1978 | Nicolosi et al. | 601/33 |
| 5,048,825 | 9/1991 | Kelly | 482/904 |
| 5,290,220 | 3/1994 | Guhl | 602/32 |

FOREIGN PATENT DOCUMENTS

| | | | |
|---|---|---|---|
| 2440187 | 5/1980 | France | 601/33 |
| 2415227 | 10/1974 | Germany | 602/36 |
| 2201353 | 9/1988 | United Kingdom | 601/33 |

Primary Examiner—Jeanne M. Clark
Attorney, Agent, or Firm—Caesar, Rivise, Bernstein, Cohen & Pokotilow, Ltd.

[57] ABSTRACT

A device for mounting onto a traction machine having a base console, an elongated standard extending upward therefrom, and an elongated traction cable suspended vertically downward from the standard and having a free end connector. The device comprises an upper arm support plate, a wrist band, and an adjustable mounting sleeve. The wrist band is arranged to be releasably secured about one wrist of a person and connected to the connection means of the traction machine to be suspended therefrom. The upper arm support plate is an elongated member releasably secured by a bracket to the sleeve for supporting the upper arm of the person and includes an adjustable strap for extending about the upper arm of the person to releasably secure it in place on support plate. The adjustable sleeve is slidably mounting on the standard and includes releasable securement means, e.g., at least one set screw, for releasably securing it at any vertical position along the standard. Thus, the person, when seated, can readily dispose his/her upper arm on the support plate irrespective of the height of the base portion of the traction machine and with his/her forearm being oriented vertically upward and with the wrist band secured about the wrist of the person, so that the machine can apply tension to the wrist to alleviate the pain caused by carpal tunnel syndrome or some other disorder of the wrist, e.g., a strain, sprain or subluxation.

10 Claims, 4 Drawing Sheets

DEVICE FOR USE ON A TRACTION MACHINE TO TREAT CARPAL TUNNEL SYNDROME AND OTHER PROBLEMS OF THE WRIST

This invention relates generally to medical equipment and more particularly to devices for use with traction equipment to treat carpal tunnel syndrome and other problems of the wrist by applying traction thereto.

Various traction machines are commercially available for applying traction to selected portions of the anatomy of a person to treating some medical condition or problem of the person. For example, Barrington Equipment Company, of Wauconda, Ill. presently markets a pneumatic traction machine, believed to be manufactured by Para Tech Industries, Inc., under the trade designation Para Tech CTD MARK I, for applying traction to the wrist of a person suffering from carpal tunnel syndrome. While this device appears suitable for its intended purposes, it leaves much to be desired from the standpoint of ease of use and patient comfort. In this regard the Para Tech CTD MARK I device comprises a console from which a post or pole projects upward. A VELCRO® wrist sleeve is connected to the post for encircling the wrist of the person to be treated while preventing any movement of the arm with respect to the post. To achieve that end the person must sit beside the machine with his or her forearm oriented horizontally at a predetermined height with respect to the machine. The machine's post is arranged to be moved away from the person by a pneumatic actuator so that the person's arm and wrist is extended, i.e., traction applied thereto. This extension or traction of the arm and wrist is said to reduce the compression of the carpal tunnel ligament upon the median nerve, whereupon the carpal bones now open to allow more room in the carpal tunnel. Since the machine is of a fixed height and since the forearm of the person being treated has to be oriented horizontally, that person must seat himself/ herself so that his/her forearm is at the predetermined appropriate height for the application of traction thereto. Depending upon the height of the person, he/she may have to sit bent or hunched over (if the machine is too low for him/her), or else sit unnaturally erect and upright (if the machine is too high for him/her) to be in the proper position for the application of traction to his/her forearm and wrist. This can result in patient discomfort or tiring, particularly for treatments requiring long duration traction.

Other traction equipment is commercially available for applying traction to parts of the body of a person. Examples of such machines are those sold under the trade designation TX by Chattanooga Corporation of Chattanooga, Tenn. While these machines are generally suitable for their intended purposes, they are not particularly configured for use in the treatment of carpal tunnel syndrome or other problems of the wrist.

OBJECTS OF THE INVENTION

Accordingly, it is a general object of this invention to provide a device which overcome the disadvantages of the prior art.

It is a further object of this invention to provide a device which can be readily attached to a conventional traction machine for applying traction to the wrist of a person.

It is a further object of this invention to provide a device for use with a conventional traction machine and which device is readily adjustable to enable it to apply traction to the wrist of a person irrespective of the height of the person.

It is still a further object of this invention to provide a device for use with a conventional traction machine, which is simple in construction.

It is still a further object of this invention to provide a device for use with a conventional traction machine, which is easy to mount on the machine and dismount from the machine.

It is yet a further object of this invention to provide a device for use with a conventional traction machine, which is easy to adjust to accommodate persons of various heights.

SUMMARY OF THE INVENTION

These and other objects of this invention are achieved by providing a device for mounting onto a traction machine comprising a base portion, an elongated standard extending upward from the base portion, and elongated suspension means suspended vertically downward from the standard and having a free end in the form of connection means for releasable securement to a portion of the body of a person. The suspension means of the traction machine is arranged to apply tension to the portion of the person's body suspended therefrom.

The device of this invention comprising upper arm support means, wrist engaging means, and adjustable sleeve means. The wrist engaging means comprising a member, e.g., a VELCRO® strap, arranged to be releasably secured about one wrist of a person and connected to the connection means of the traction machine to be suspended therefrom. The upper arm support means comprising an elongated member, e.g., a plate, for horizontally supporting the upper arm of the person and having means for releasably securing the upper arm in place thereon.

The sleeve means is arranged for slidable mounting on the standard and includes releasable securement means for releasably securing the sleeve means at any vertical position along the standard. The sleeve means mounts the support means horizontally thereon with respect to the standard, whereupon the sleeve means can be readily positioned at any vertical position along the standard and secured in place thereat so that the person, when seated, can readily dispose his/her upper arm horizontally on the support member irrespective of the height of the base portion of the traction machine and with his/her forearm being oriented vertically upward. Accordingly, the wrist engaging means can then be secured to the wrist of the vertically extending forearm of the person, whereupon tension can be applied thereto.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF A PREFERRED EMBODIMENT

Figure 1:
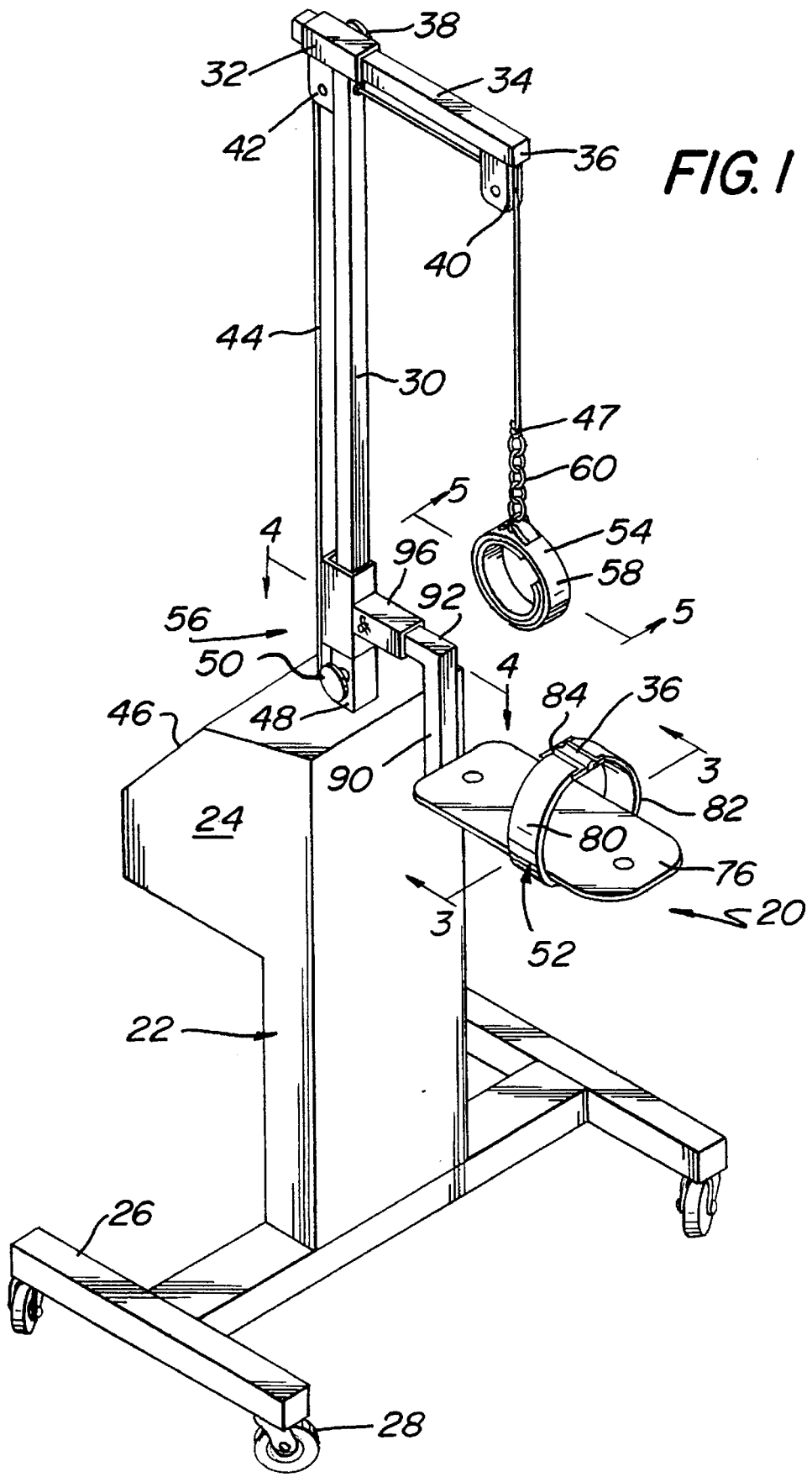
FIG. 1 is an isometric view of one preferred embodiment of device constructed in accordance with this invention for mounting onto a conventional traction machine.

Referring now to various figures of the drawing where like reference numerals refer to like parts, in FIG. 1 there is shown generally at 20 a device constructed in accordance with this invention for use with a conventional traction machine 22, e.g., a cervical spine machine like the TX cervical traction unit sold by Chattanooga Corporation, or as a part of a specially constructed traction machine.

Before describing the details of the device 20 a short description of the conventional cervical traction unit 22 is in order. That unit basically comprises a console 24 mounted on a base 26. In the embodiment shown the base includes casters 28 to facilitate the movement of the unit to a desired location. A tubular post or upright 30 of square cross section extends vertically upward from the top of the console 24 and terminates at its top end in a bracket 32. The bracket 32 is fixedly secured to the post and includes a square passageway extending horizontally therethrough for sliding receipt of a tubular cross bar 34 so that the free end 36 of the cross bar can be extended any desired distance from the upright 30. A set screw 38 having an enlarged head extends through the bracket 32 for frictionally engaging a portion of the side of the cross bar extending through the bracket to lock the cross bar in place at the desired extended position.

A bracket-mounted pulley 40 is located at the free end 36 of the crossbar 34. A similar pulley 42 is mounted on the bracket 30 of the upright 30. A flexible, tension cable 44 extends upward from a prime mover (not shown) inside the console 24 along the upright 30, over the pulley 42, along the cross bar 34, and over the pulley 40. The free end 47 of the cable is arranged to be secured to a chain forming a portion of the device of the subject invention. The cable is arranged to be retracted or pulled inward into the console at a controlled tension by the operation of the prime mover located therein, as is conventional. This action applies traction to any portion of a patient's body to which the free end 47 of the cable is connected. The amount of tension or traction applied to the patient, as well as other operating parameters of the machine 22, are established by the setting of various control knobs and/or buttons (not shown) on the sloping front panel 46 of the machine's console 24.

The height of the post or upright 30, i.e., the amount that it extends out of the console 24, is adjustable by means of a mounting bracket 48. The mounting bracket 48 is similar to bracket 30 and is fixedly mounted on the top panel of the console 24. The bracket 48 includes a passageway communicating with the interior of the console and through which the lower end of the post 30 slidably extends. An enlarged head set screw 50 extends through the bracket 48 for frictionally engaging a side wall portion of the post to releasably secure the post in place at the desired extended height.

As mentioned earlier the device 20 can form a portion of a specially designed traction machine, or can be an attachment unit which is arranged to be used with existing traction machines, like the cervical spine unit described earlier. In such a later case the device effectively retrofit a conventional cervical spine traction machine into a wrist traction machine. Moreover, the device 20 is preferably portable so that it can be readily mounted onto, e.g., attached to, the machine 20 when desired, and removed from the machine when it is not needed further. Thus, a single device 20 can service plural machines 22.

In any case the device 20 provides horizontal support for the upper arm of the person to be treated so that tension or traction can be provided vertically to the wrist and forearm of the person. The device 20 basically comprises an upper arm rest or support subassembly 52, a wrist engaging subassembly 54, and adjustable mounting subassembly 56.

Figure 5:
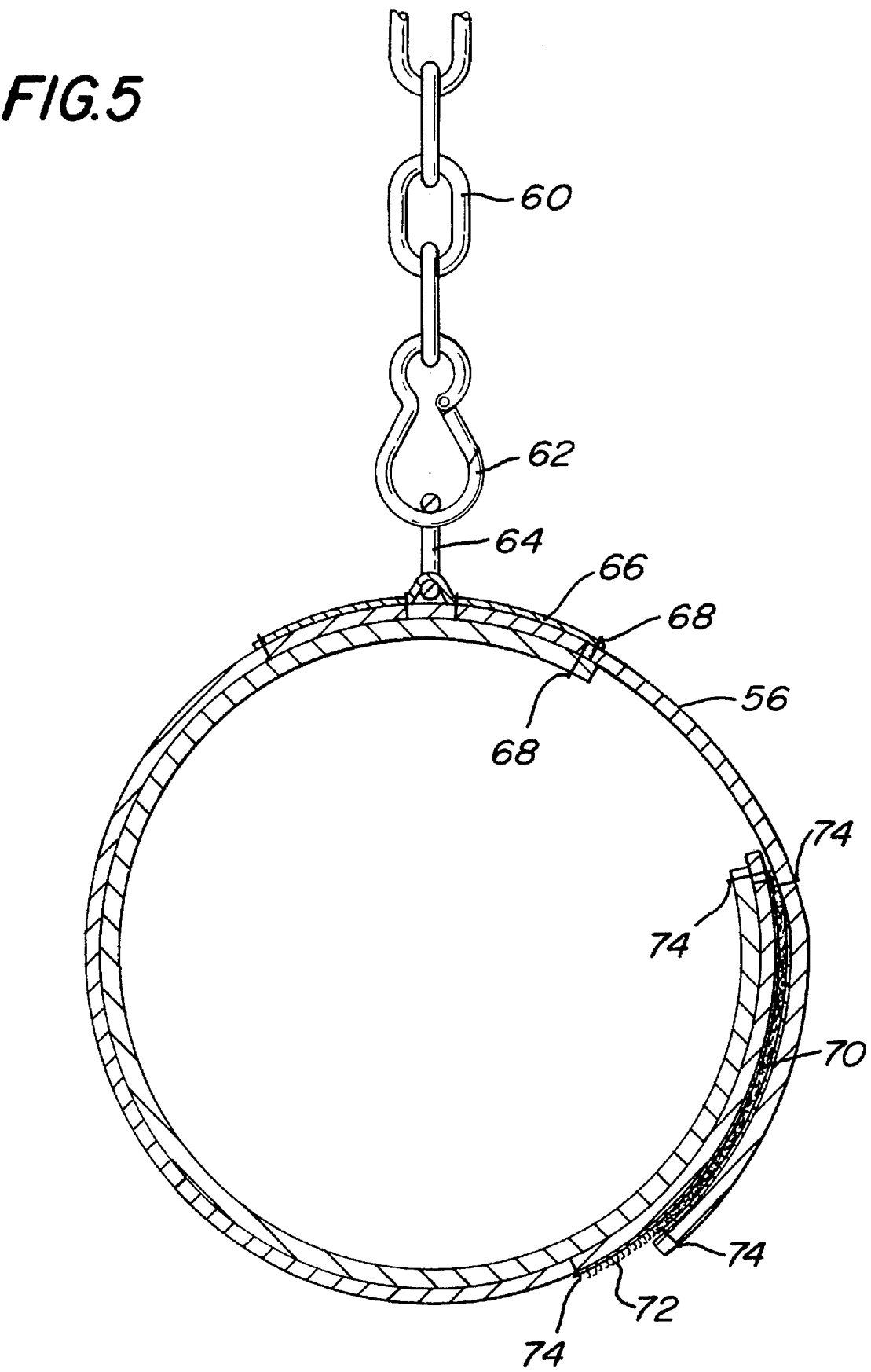
FIG. 5 is an enlarged sectional view taken along line 5—5 of FIG. 1.

As best seen in FIG. 5 the wrist engaging subassembly 54 basically comprises a flexible strap 58, a portion of which is in two layers, and a connector chain 60. The strap 58 is arranged to be wrapped about and releasably secured to the wrist (FIG. 2) of the person to be treated. The connector chain includes plural links and has a clasp 62 at its lower end. The clasp 62 is arranged to releasably engage a loop or ring 64 pivotally secured to the strap 58 by a mounting strip 66. The mounting strip is sewn to the strap 58 by a line of stitches 68, thereby fixedly securing the ring 64 to the strap 58, albeit enabling the ring to pivot with respect thereto. The link at the upper end of the chain 60 is secured to the free end 56 of the cable 44 to suspend the chain from the cable. In particular, the free end of the cable is looped through the upper-most link of the chain 60 and is knotted to secure it to the cable.

The strap 58 is formed of any suitable flexible material, e.g., fabric, plastic, or leather, and includes a pair of engaging VELCRO® patches 70 and 72 fixedly secured, e.g., sewn by stitches 74, to respective portions of the strap so that the strap can be wrapped closely, yet comfortably, around the person's wrist, irrespective of the size of the person. The VELCRO® patches releasably engage each other to hold the strap in place.

Figure 2:
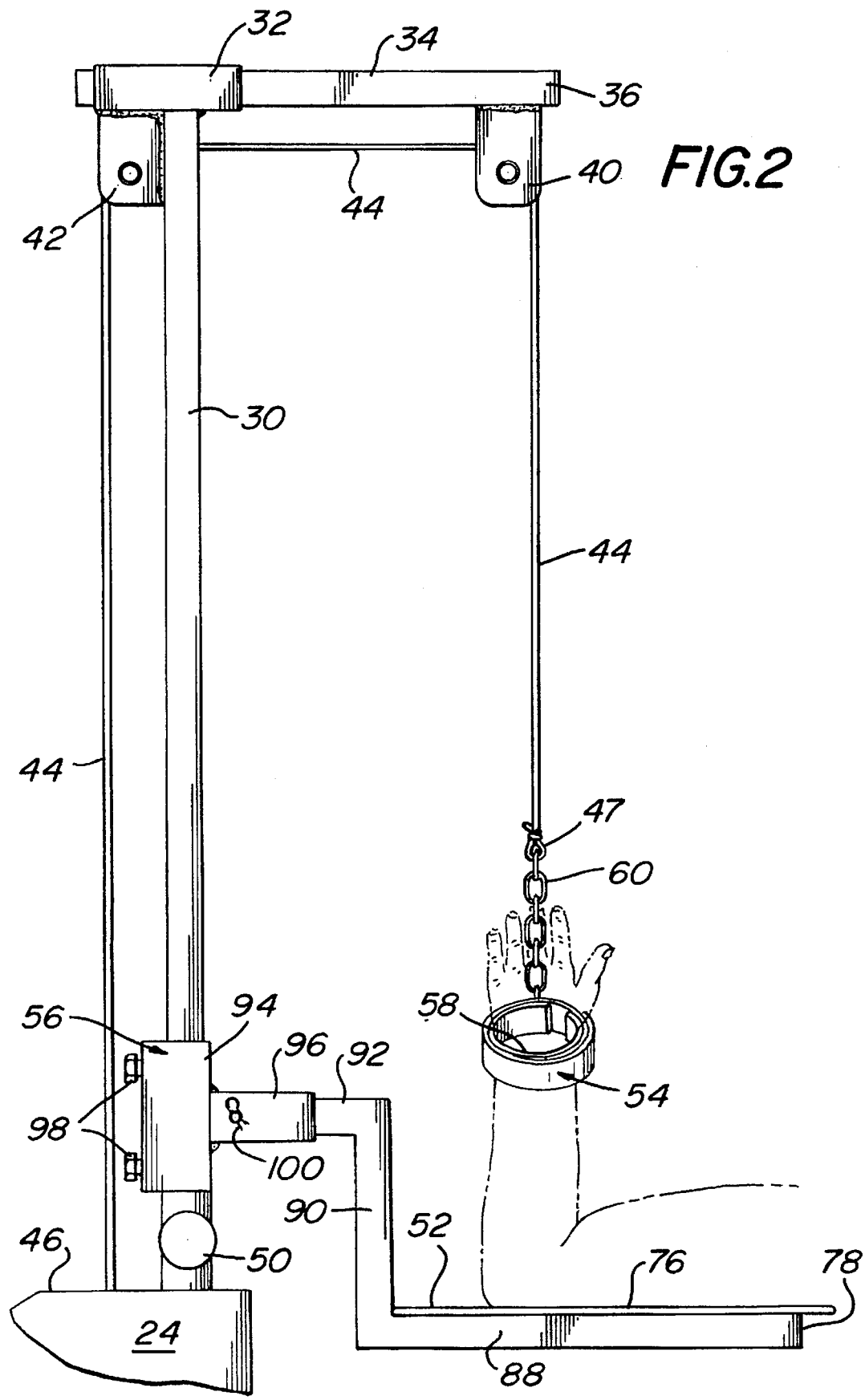
FIG. 2 is an enlarged side elevational view of the device shown in FIG. 1 in use for applying traction to the wrist of a person for treating carpal tunnel syndrome and other problems of the wrist.

The upper arm support subassembly or arm rest 52 is arranged to support the person's upper arm horizontally, while the person's forearm is generally upright and his/er wrist is suspended from the cable 44, via the subassembly 54, like shown in FIG. 2. It should be noted at this juncture that the person's forearm need not be perfectly vertical, so long as it is directed generally upward. When so directed the tension applied by the retraction of the cable effects the extension or traction of the person's wrist.

Figure 3:
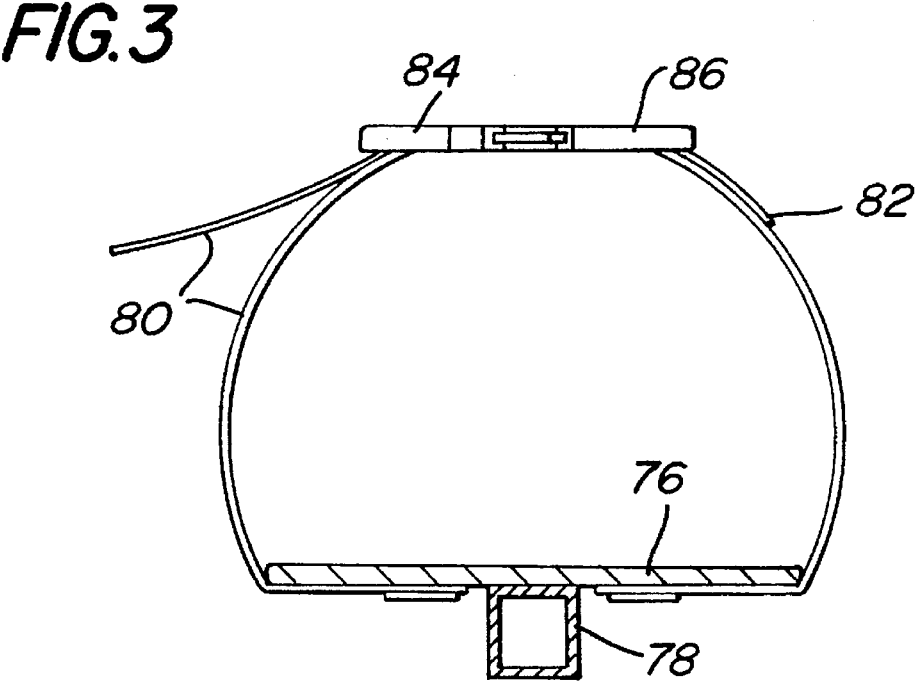
FIG. 3 is an enlarged sectional view taken along line 3—3 of FIG. 1.
Figure 4:
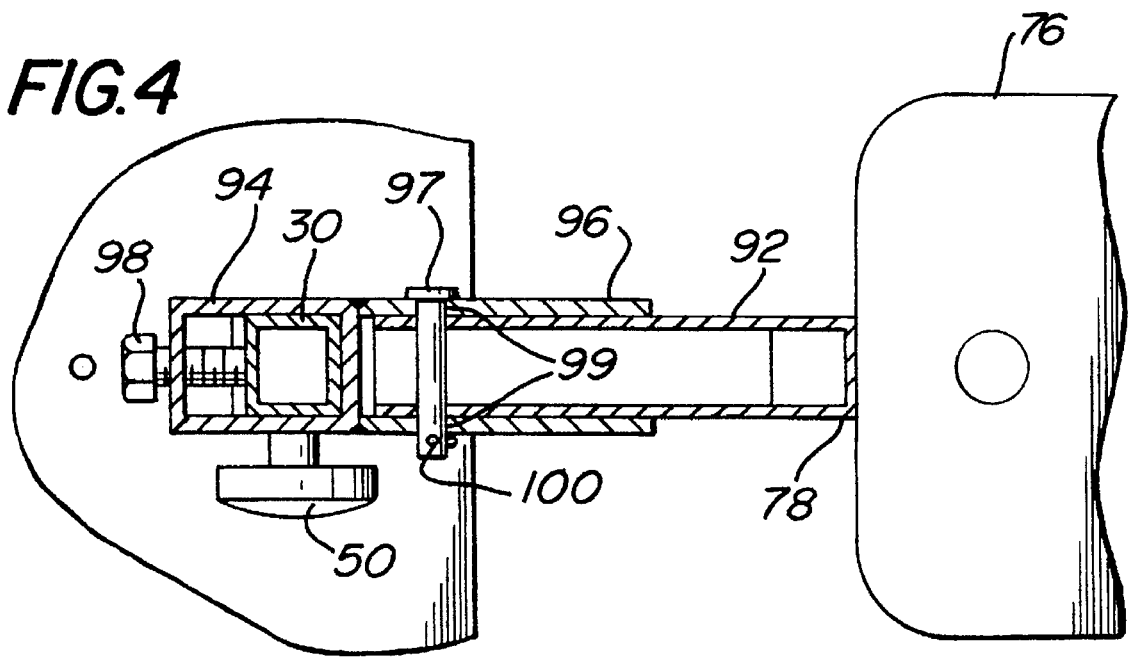
FIG. 4 is an enlarged sectional view taken along line 4—4 of FIG. 1.

As can best be seen in FIGS. 2–4 the upper arm support subassembly or arm rest 52 basically comprises an elongated, generally planar support plate 76, a support bar or frame 78, and a pair of arm-mounting straps 80 and 82. The support bar will be described in detail later. Suffice it for now to state that it is a tubular member of square cross section formed of a strong material, e.g., steel. The frame includes a linear end portion (to be described later) to which the support plate is fixedly secured by any suitable means, e.g., fasteners, adhesives, etc., so that the plate is oriented horizontally. The support plate is arranged for supporting the upper arm of the person horizontally thereon. The arm-mounting straps are arranged for releasably securing the person's upper arm in place on the support plate 76. To that end each strap includes one end which is fixedly secured to the underside of the plate 76, as shown clearly in FIG. 3. The other end portion of the strap 80 includes a buckle 84 slidably mounted thereon, while the other end of the strap 82 includes a buckle 86 fixedly mounted thereon. The buckles 84 and 86 are arranged for releasable securement to each other. Thus, the two straps 80 and 82 can be secured to each other and the end portion of the strap 80 pulled to adjust the size of the resulting band or loop (shown in FIG. 3) to closely, yet comfortably, surround the upper arm of the person when it is disposed on the top surface of the support plate 76.

The support bar or frame 78, as mentioned earlier, is a tubular member which includes the linear portion 88 upon which the support plate 76 is fixedly mounted, an intermediate portion 90, and an off-set end portion 92. The offset end portion 92 extends parallel to the linear portion 88 and is arranged to be releasably secured to the adjustable mounting subassembly 56 to releasably secure the upper armsupport subassembly onto the machine's upright or post 30 at any desired height.

As can be seen clearly in FIGS. 2 and 4 the adjustable mounting subassembly 56 basically comprises a sleeve 94 and an associated bracket 96. The sleeve 94 is arranged for slidable mounting on the upright or post 30 of the machine 22, and includes releasable securement means in the form of a pair of set screws 98 extending therethrough for releasably securing, e.g., frictionally engaging, the post 30 irrespective of the vertical position of the sleeve 94 thereon. The bracket 96 is a hollow member fixedly secured, e.g., welded, to a sidewall of the sleeve 94, and is oriented horizontally to receive the free end of the offset portion 92 of the support bar 78. An enlarged head pin 97 (FIG. 4) extends through aligned holes 99 in the bracket 96 and in the free end of the offset portion 92 of the support bar to hold the support bar in place. A locking clip 100 extends through a hole in the pin 97 opposite its enlarged head to prevent the pin from accidentally sliding out of the aligned holes.

By releasing the set screws 98 the sleeve 94 (and the upper arm support subassembly or arm rest 52) mounted thereon can be slid up or down the upright or post 30 so that the upper arm support plate is at the desired elevation to comfortably support the upper arm of the person being treated. Once in that position the set screws can be tightened to hold the sleeve in place. Since the support bar 78 is offset, the support plate can be lowered to a position below the top surface of the console, to accommodate very small persons. Accordingly, any person, when seated on means (not shown) beside the machine 22, can readily dispose his/her upper arm horizontally on the support member irrespective of the height of the console portion of the machine, and with his/her forearm being oriented upward in a comfortable position so that the wrist strap can be placed about the wrist so that tension can be applied to the wrist by the retraction of the cable 44.

As should be appreciated from the foregoing the device 20 of this invention provides various features so that when used with a traction machine (or made part of a traction machine) it places sufficient traction on the carpal ligament, while separating the carpal bones to take pressure off of the median nerve, thereby reducing the symptoms of carpal tunnel syndrome. It should be pointed out at this juncture that the subject invention is not limited for use in treating carpal tunnel syndrome. Thus, it can be used to treat other medical problems of the wrist, such as strains, sprains, subluxations, edema, general wrist tenderness and aches, vascular insufficiency and/or neurologia, muscle weakness due to carpal mobility, and to relieve pain due to arthritis, while slowing down its future progression. In addition, the subject invention can be used prophylactically, e.g., as preventive maintenance of the wrist joint.

In addition to the foregoing medical advantages, the subject invention exhibits a number of other advantageous features. In this regard, since it is may be formed as a portable unit, it can be readily mounted on a conventional cervical spine traction machine when desired, thereby resulting in substantial economy of use, e.g., a single unit can be used on multiple traction machines.

Moreover, since the device 20 is fully adjustable it allows for maximum biomechanical traction without undue patient discomfort. For example, the arm rest is fully adjustable to allow for maximum biomechanical traction for all ages and sizes of people. The length of the traction chain is adjustable, also in the interest of patient comfort. The strap on the upper arm is adjustable for maximum stability and bracing. Moreover, only a single strap is necessary to immobilize the upper arm, with no strap (and hence no compression) of the forearm.

Since traction is applied in a generally vertically or upright orientation, the forearm angle is free to assume the most relaxed orientation with respect to the vertical axis. This enables optimum carpal traction due to the relation of the flexor and extensor tendons and muscles. Moreover, the application of traction upright or vertically ensures that there is little or no friction on forearm from the elbow to the wrist. Further still, the traction is applied to the radius and ulna, as well as the carpal bones, all without applying pressure on the shoulder.

Without further elaboration, the foregoing will so fully illustrate our invention that others may, by applying current or future knowledge, adopt the same for use under various conditions of service.

What we claim is:

1. A device for use in combination with a traction machine, said device being arranged for mounting onto the traction machine, the traction machine comprising a base portion, an elongated standard extending upward from the base portion, and elongated flexible suspension means suspended vertically downward from the standard and having a free end in the form of connection means for releasable securement to a wrist of a person, the person having an upper arm, and a forearm connected thereto terminating in a hand, the wrist being located between the hand and the forearm, the forearm and upper arm each having a respective longitudinal axis, the suspension means being arranged to apply tension to the wrist along the longitudinal axis of the forearm, said device comprising upper arm support means, wrist engaging means, and adjustable sleeve means, said wrist engaging means comprising a member arranged to be releasably secured about the wrist leaving the hand free, said wrist engaging member being connected to the connection means of the traction machine to be suspended vertically therefrom, said upper arm support means comprising an elongated member for supporting the upper arm in a horizontal orientation wherein the longitudinal axis of the upper arm is horizontal and having means for releasably securing the upper arm in place thereon in said horizontal orientation, said sleeve means being arranged for slidable mounting on the standard and including releasable securement means for releasably securing said sleeve means at any vertical position along the standard, said sleeve means mounting said upper arm support means horizontally with respect to the standard, whereupon said sleeve means can be readily slidably positioned at any vertical position along the standard and secured in place thereat so that the person, when seated, can readily dispose the upper arm in said horizontal orientation on said upper arm support member to be held immobile in that position irrespective of the height of the base portion of the traction machine and with the longitudinal axis of the forearm being oriented vertically upward and with said wrist engaging means being secured to the wrist, whereupon tension can be applied to the wrist but not to the hand by the flexible suspension means in a direction parallel to the longitudinal axis of the forearm and perpendicular to the longitudinal axis of the upper arm.

2. The device of claim 1 wherein said sleeve means includes bracket means for releasably mounting said upper arm support means thereon.

3. The device of claim 1 wherein said releasable securement means of said sleeve means comprises at least one set screw extending through a portion of said sleeve means and into engagement with a portion of the standard.

4. The device of claim 2 wherein said bracket means comprises a removable pin for releasably mounting said upper arm support means thereon.

5. The device of claim 1 wherein the means for releasably securing the upper arm of the person on said upper arm support means comprises a strap arranged to be extended about a portion of the upper arm of the person.

6. The device of claim 1 wherein said strap is adjustable in size to accommodate various sized upper arms.

7. The device of claim 6 wherein said strap includes adjustable buckle means for enabling said strap to be held in place extended about the upper arm of the person.

8. The device of claim 1 wherein said wrist engaging means, comprises a strap arranged to be extended about the wrist of the person.

9. The device of claim 8 wherein said strap is adjustable in size to accommodate various sized wrists.

10. The device of claim 9 wherein said strap includes cooperating releasably securable hook and loop fastening means.

* * * * *